(12) United States Patent
Bradley

(10) Patent No.: US 8,594,785 B2
(45) Date of Patent: Nov. 26, 2013

(54) NEUROSTIMULATION SYSTEM AND METHOD FOR MEASURING PATIENT ACTIVITY

(75) Inventor: Kerry A. Bradley, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1283 days.

(21) Appl. No.: 12/024,947

(22) Filed: Feb. 1, 2008

(65) Prior Publication Data

US 2008/0188909 A1     Aug. 7, 2008

Related U.S. Application Data

(60) Provisional application No. 60/887,794, filed on Feb. 1, 2007.

(51) Int. Cl.
*A61N 1/37*     (2006.01)

(52) U.S. Cl.
USPC .............................................................. 607/8

(58) Field of Classification Search
USPC ..................................... 607/8, 17–18, 28–29
See application file for complete search history.

(56) References Cited

U.S. PATENT DOCUMENTS

| | | | |
|---|---|---|---|
| 3,646,940 A | 3/1972 | Timm et al. | |
| 3,724,467 A | 4/1973 | Avery et al. | |
| 4,291,699 A | 9/1981 | Geddes et al. | |
| 4,686,987 A | 8/1987 | Salo et al. | |
| 4,735,204 A | 4/1988 | Sussman et al. | |
| 5,027,813 A * | 7/1991 | Pederson et al. ................ 607/19 |
| 5,168,871 A | 12/1992 | Grevious | |
| 5,190,035 A | 3/1993 | Salo et al. | |
| 5,282,840 A | 2/1994 | Hudrlik | |
| 5,333,618 A | 8/1994 | Lekhtman et al. | |
| 5,372,607 A | 12/1994 | Stone et al. | |
| 5,483,969 A | 1/1996 | Testerman et al. | |
| 5,485,851 A | 1/1996 | Erickson | |
| 5,522,862 A | 6/1996 | Testerman et al. | |
| 5,540,729 A | 7/1996 | Weijand | |

(Continued)

FOREIGN PATENT DOCUMENTS

| WO | WO 95/00201 A1 | 1/1995 |
|---|---|---|
| WO | WO 00/13585 A1 | 3/2000 |
| WO | WO 2006/013585 A1 | 2/2006 |

OTHER PUBLICATIONS

PCT International Search Report for PCT/US2008/052851, Applicant: Boston Scientific Neuromodulation Corporation, Form PCT/ISA/210 and 220, dated Jun. 24, 2008 (5 pages.).

(Continued)

*Primary Examiner* — Amanda Patton
(74) *Attorney, Agent, or Firm* — Vista IP Law Group LLP

(57) ABSTRACT

Electrical energy is conveyed via an implanted tissue stimulation system into tissue of the patient over a period of time. Electrical parameter data (e.g., impedance data and/or field potential data) is measured based on the electrical energy conveyed into the tissue of the patient, whereby the electrical parameter data is modulated in response to the physical activity of the patient to generate a time-varying signal (e.g., an oscillating signal). The time-varying signal is analyzed, and the physical activity of the patient (e.g., the physical activity level of the patient or the physical events performed by the patient) is tracking during the time period based on the analyzed time-varying signal.

45 Claims, 4 Drawing Sheets

(56) References Cited

U.S. PATENT DOCUMENTS

| | | | |
|---|---|---|---|
| 5,540,733 A | 7/1996 | Testerman et al. | |
| 5,546,952 A | 8/1996 | Erickson | |
| 5,549,655 A | 8/1996 | Erickson | |
| 5,593,431 A | 1/1997 | Sheldon | |
| 5,735,887 A | 4/1998 | Barreras, Sr. et al. | |
| 5,782,890 A | 7/1998 | Wahlstrand et al. | |
| 5,824,029 A | 10/1998 | Weijand et al. | |
| 5,895,416 A | 4/1999 | Barreras, Sr. et al. | |
| 5,931,858 A | 8/1999 | Kadhiresan et al. | |
| 5,991,661 A | 11/1999 | Park et al. | |
| 6,015,388 A | 1/2000 | Sackner et al. | |
| 6,044,297 A | 3/2000 | Sheldon et al. | |
| 6,246,912 B1 | 6/2001 | Sluijter et al. | |
| 6,516,227 B1 | 2/2003 | Meadows et al. | |
| 6,609,029 B1 | 8/2003 | Mann et al. | |
| 6,714,892 B2 | 3/2004 | Houge et al. | |
| 6,741,892 B1 | 5/2004 | Meadows et al. | |
| 6,922,585 B2 * | 7/2005 | Zhou et al. | 600/518 |
| 6,937,900 B1 * | 8/2005 | Pianca et al. | 607/19 |
| 6,993,384 B2 | 1/2006 | Bradley et al. | |
| 7,039,462 B2 | 5/2006 | Pastore et al. | |
| 7,167,743 B2 * | 1/2007 | Heruth et al. | 600/509 |
| 7,177,684 B1 | 2/2007 | Kroll et al. | |
| 7,313,440 B2 | 12/2007 | Miesel | |
| 7,317,948 B1 | 1/2008 | King et al. | |
| 7,330,760 B2 | 2/2008 | Heruth et al. | |
| 7,353,064 B2 | 4/2008 | Gliner et al. | |
| 7,447,545 B2 | 11/2008 | Heruth et al. | |
| 7,539,538 B2 | 5/2009 | Parramon et al. | |
| 2003/0139781 A1 | 7/2003 | Bradley et al. | |
| 2005/0267546 A1 | 12/2005 | Parramon et al. | |
| 2006/0161225 A1 | 7/2006 | Sormann et al. | |
| 2006/0195159 A1 | 8/2006 | Bradley et al. | |
| 2007/0038250 A1 | 2/2007 | He et al. | |
| 2007/0142874 A1 | 6/2007 | John | |
| 2008/0188909 A1 | 8/2008 | Bradley | |

OTHER PUBLICATIONS

PCT Written Opinion of the International Search Authority for PCT/US2008/052851, Applicant: Boston Scientific Neuromodulation Corporation, Form PCT/ISA/237, dated Jun. 24, 2008 (5 pages).

PCT International Preliminary Report on Patentability (Chapter I of the Patent Cooperation Treaty) for PCT/US2008/052851, Applicant: Boston Scientific Neuromodulation Corporation, Form PCT/IB/326 and 373, dated Aug. 13, 2009 (7 pages).

Office Action dated Nov. 5, 2010 in Australian Application No. 2008210293, Applicant: Boston Scientific Neuromodulation Corporation, (2pages).

Office Action dated Jan. 12, 2011 in Australian Application No. 2008210293, Applicant: Boston Scientific Neuromodulation Corporation, (2pages).

Office Action dated May 10, 2011 in Australian Application No. 2008210293, Applicant: Boston Scientific Neuromodulation Corporation, (2pages).

Office Action dated Jun. 27, 2011 in European Application No. 08728869.2-2305, Applicant: Boston Scientific Neuromodulation Corporation, (3pages).

Office Action drafted on May 2, 2012 for Japanese Patent Application No. 2009-548482, Applicant: Boston Scientific Neuromodulation Corporation, (3pages); with translations prepared by Nakamura & Partners (4pages).

Office Action dated Apr. 5, 2013 for Canadian Patent Application No. 2677122, Applicant: Boston Scientific Neuromodulation Corporation, (4pages).

* cited by examiner

NEUROSTIMULATION SYSTEM AND METHOD FOR MEASURING PATIENT ACTIVITY

RELATED APPLICATION DATA

The present application claims the benefit under 35 U.S.C. §119 to U.S. Provisional Patent Application Ser. No. 60/887,794, filed Feb. 1, 2007. The foregoing application is incorporated by reference into the present application in its entirety for all purposes.

FIELD OF THE INVENTION

The present invention relates to tissue stimulation systems, and more particularly, to a system and method for measuring the physical activity of a patient implanted with a tissue stimulation system.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems such as the Freehand system by NeuroControl (Cleveland, Ohio) have been applied to restore some functionality to paralyzed extremities in spinal cord injury patients.

Each of these implantable neurostimulation systems typically includes an electrode lead implanted at the desired stimulation site and an implantable pulse generator (IPG) implanted remotely from the stimulation site, but coupled either directly to the electrode lead or indirectly to the electrode lead via a lead extension. Thus, electrical pulses can be delivered from the IPG to the electrode lead to stimulate the tissue and provide the desired efficacious therapy to the patient.

In certain scenarios, it may be desirable to track the physical activity (e.g., activity level or body manipulations) of the patient that has received the implantable neurostimulation system, which provides an indication of the efficacy of the therapy provided by the stimulation system; that is, the more efficacious the therapy, the more diurnally active the patient will be. Thus, knowledge of the physical activity of the patient over a period of time in which therapeutic stimulation is applied to the patient may be used by a physician or clinician to prescribe drugs, reprogram or upgrade the IPG, or implement or modify other therapeutic regimens (such as physical or occupational therapy). Knowledge of the physical activity of the patient may also be used to adapt the therapy provided by the stimulation system in real time, so that the stimulation is consistently provided to the patient at an efficacious and/or comfortable level.

There, thus, remains a need for an improved method and system for determining the physical activity of a patient in which a neurostimulation system has been implanted.

SUMMARY OF THE INVENTION

In accordance with a first aspect of the present inventions, a method of providing therapy to a patient is provided. The method comprises conveying electrical energy from an implanted tissue stimulation system into tissue of the patient over a period of time. The electrical energy conveyed from the tissue stimulation device may provide the therapy to the patient or may constitute electrical energy independent of the therapy. The method further comprises measuring electrical parameter data (e.g., impedance data and/or field potential data) based on the electrical energy conveyed into the tissue of the patient, whereby the electrical parameter data is modulated in response to the physical activity of the patient to generate a time-varying signal (e.g., an oscillating signal).

The method further comprises analyzing the time-varying signal. In one optional method, the time-varying signal analysis comprises determining a magnitude of the time-varying signal; for example, by detecting a peak-to-peak amplitude values of the time-varying signal or detecting an energy of the time-varying signal. In another optional method, the time-varying signal analysis comprises determining a morphology of the time-varying signal; for example, by detecting an envelope of the time-varying signal. The method further comprises tracking the physical activity of the patient (e.g., the physical activity level of the patient or the physical events performed by the patient) during the time period based on the analyzed noise. An optional method comprises modifying therapy provided to the patient by the stimulation device based on the tracked physical activity.

In accordance with a second aspect of the present inventions, a tissue stimulation system is provided. The tissue stimulation system comprises an implantable electrode lead and an implantable electrical stimulation device configured for being coupled to the electrode lead. The electrical stimulation device is configured for conveying electrical energy from the electrode lead into tissue of a patient over a period of time. The electrical energy conveyed from the electrode lead may provide therapy to the patient or may be conveyed independent of the therapy. The electrical stimulation device is also configured for measuring electrical parameter data based on the electrical energy conveyed into the tissue of the patient, whereby the electrical parameter data is modulated in response to the physical activity of the patient to generate a time-varying signal.

The system further comprises a processing device configured for analyzing the time-varying signal and tracking the physical activity of the patient (e.g., the physical activity level of the patient or the physical events performed by the patient) during the time period based on the analyzed noise. In one embodiment, the processing device is the stimulation device. In another embodiment, the processing device is an external programmer configured for communicating with the stimulation device. The time-varying signal analysis may be performed in the same manner described above.

In accordance with a third aspect of the present inventions, an electrical stimulation device implantable within a patient is provided. The stimulation device comprises one or more electrical contacts configured for coupling to one or more electrodes, and control circuitry configured for conveying electrical energy to the contact(s) for a period of time. The stimulation device further comprises monitoring circuitry configured for measuring electrical parameter data based on the electrical energy conveyed into the tissue of the patient, whereby the electrical parameter data is modulated in response to the physical activity of the patient to generate a time-varying signal. The electrical energy conveyed to the electrical contact(s) may provide therapy to the patient or may be conveyed independent of the therapy providing electrical energy. The stimulation device further comprises processing circuitry configured for analyzing the time-varying signal and tracking the physical activity of the patient (e.g., the physical activity level of the patient or the physical events performed by the patient) during the time period based on the analyzed noise. The time-varying signal analysis can be performed in the same manner described above.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG), radio frequency (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical and deep brain stimulator, peripheral nerve stimulator, or in any other neural stimulator configured to treat urinary incontinence, sleep apnea, shoulder sublaxation, etc.

Figures 1, 2:
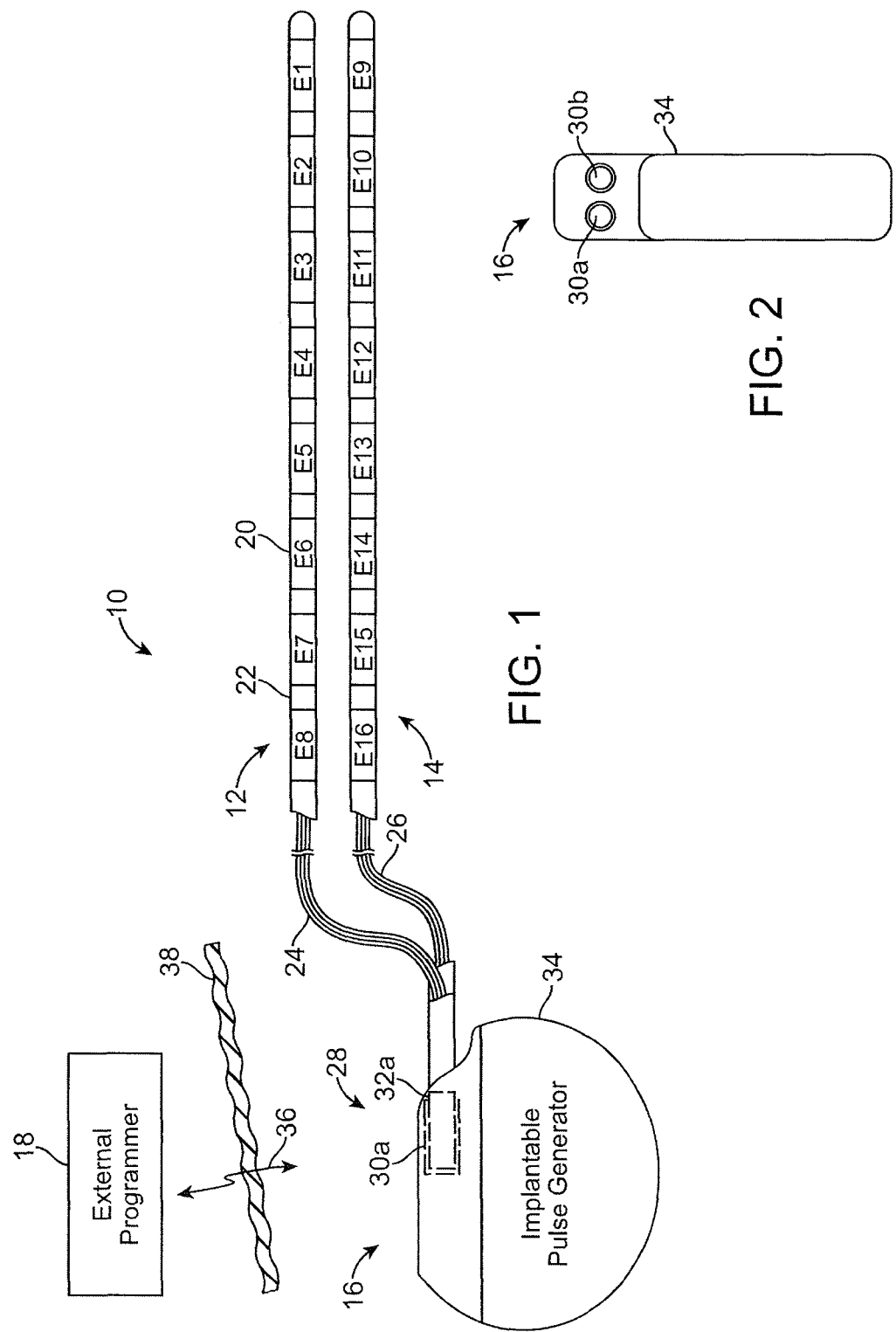
FIG. 1 is plan view of one embodiment of a spinal cord stimulation (SCS) system arranged in accordance with the present inventions.
FIG. 2 is a profile view of an implantable pulse generator (IPG) used in the SCS system of FIG. 1.

Turning first to FIGS. 1 and 2, an exemplary SCS system 10 generally includes first and second implantable neurostimulation leads 12, 14, an implantable pulse generator (IPG) 16, and an external (non-implanted) programmer 18. In the illustrated embodiment, the leads 12, 14 are percutaneous leads and, to that end, both of the leads comprise a plurality of in-line electrodes 20 carried on a flexible body 22. Alternatively, the leads 12, 14 may be replaced with a single paddle electrode lead. In the illustrated embodiment, the first lead 12 has eight electrodes 20 (labeled E1-E8), and the second lead 14 includes eight electrodes 20 (labeled E9-E16). The actual number of leads and electrodes will, of course, vary according to the intended application.

The IPG 16 is capable of directing electrical stimulation energy to each of the electrodes 20. To that end, the electrodes 20 of the first lead 12 are electrically connected to the IPG 16 by respective signal wires 24 (some of which are not shown) that extend through, or are embedded in, the associated flexible lead body 22. Similarly, the electrodes 20 of the second lead 14 are electrically connected to the IPG 16 by respective wires 26 (some of which are not shown). The signal wires 24, 26 are connected to the IPG 16 by way of an interface 28. The interface 28 may be any suitable device that allows the leads 12, 14 to be removably or permanently electrically connected to the IPG 16. Such an interface may, for example, be an electro-mechanical connector arrangement including lead connectors 30a, 30b within the IPG 16 that are configured to mate with corresponding connectors (only connector 32a is shown) on the corresponding leads 12, 14. Alternatively, the leads 12, 14 can share a single connector that mates with a corresponding connector on the IPG 16. Exemplary connector arrangements are disclosed in U.S. Pat. Nos. 6,609,029 and 6,741,892, which are incorporated herein by reference. The IPG 16 includes an outer case 34 formed from an electrically conductive, biocompatible material, such as titanium and, in some instances, will function as an electrode. The case 34 forms a hermetically sealed compartment wherein the electronic and other components (described in further detail below) are protected from the body tissue and fluids.

The IPG 16 is typically programmed, or controlled, through the use of the external programmer 18. The external programmer 18 is coupled to the IPG 16 through a suitable communications link (represented by the arrow 36) that passes through the patient's skin 38. Suitable links include, but are not limited to radio frequency (RF) links, inductive links, optical links, and magnetic links. The programmer 18 or other external device may also be used to couple power into the IPG 16 for the purpose of operating the IPG 16 or replenishing a power source, such as a rechargeable battery, within the IPG 16. Once the IPG 16 has been programmed, and its power source has been charged or otherwise replenished, the IPG 16 may function as programmed without the external programmer 18 being present.

With respect to the stimulus patterns provided during operation of the SCS system 10, electrodes that are selected to transmit or receive stimulation energy are referred to herein as "activated," while electrodes that are not selected to transmit or receive stimulation energy are referred to herein as "nonactivated." Electrical stimulation will occur between two (or more) electrodes, one of which may be the IPG case 34, so that the electrical current associated with the stimulus has a path from the energy source contained within the IPG case 34 to the tissue and a return path from the tissue to the energy source contained within the case 34. Simulation energy may be transmitted to the tissue in a monopolar or multipolar (e.g., bipolar, tripolar, etc.) fashion.

Monopolar stimulation occurs when a selected one of the lead electrodes 20 is activated along with the case 34, so that stimulation energy is transmitted between the selected electrode 20 and case 34. Bipolar stimulation occurs when two of the lead electrodes 20 are activated as anode and cathode, so that stimulation energy is transmitted between the selected electrodes 20. For example, electrode E3 on the first lead 12 may be activated as an anode at the same time that electrode E11 on the second lead 14 is activated as a cathode. Tripolar stimulation occurs when three of the lead electrodes 20 are activated, two as anodes and the remaining one as a cathode, or two as cathodes and the remaining one as an anode. For example, electrodes E4 and E5 on the first lead 12 may be activated as anodes at the same time that electrode E12 on the second lead 14 is activated as a cathode.

Figure 3:
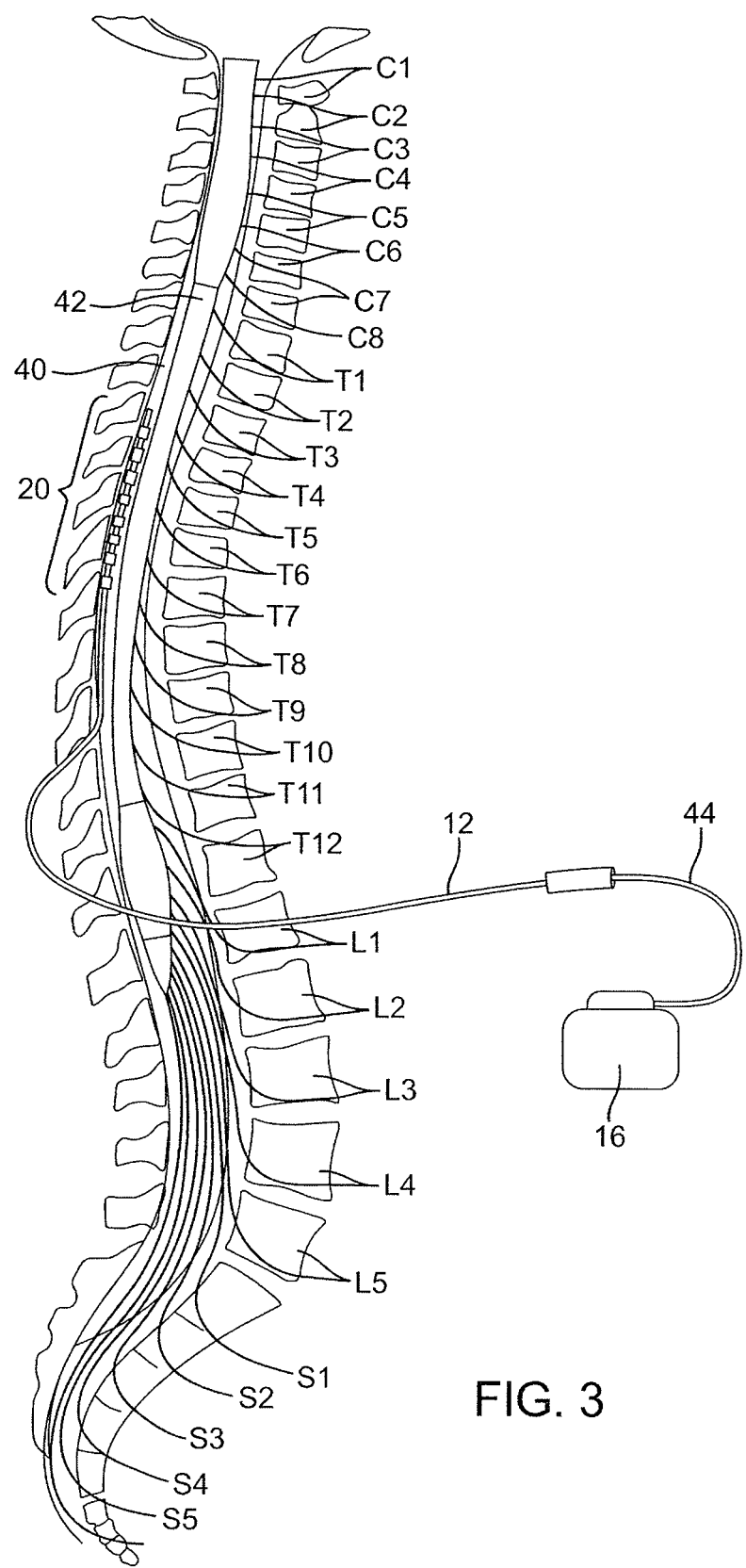
FIG. 3 is a plan view of the SCS system of FIG. 1 in use with a patient.

As shown in FIG. 3, the neurostimulation leads 12, 14 (only lead 12 shown) are implanted within the in the epidural space 40 of a patient through the use of a percutaneous needle or other convention technique, so as to be in close proximity to the spinal cord 42. Once in place, the electrodes 20 may be used to supply stimulation energy to the spinal cord 42 or nerve roots. The preferred placement of the leads 12, 14 is such, that the electrodes 20 are adjacent, i.e., resting upon, the nerve area to be stimulated. Due to the lack of space near the location where the leads 12, 14 exit the epidural space 40, the IPG 16 is generally implanted in a surgically-made pocket either in the abdomen or above the buttocks. The IPG 16 may, of course, also be implanted in other locations of the patient's body. A lead extension 44 may facilitate locating the IPG 14 away from the exit point of the leads 12, 14.

Figure 4:
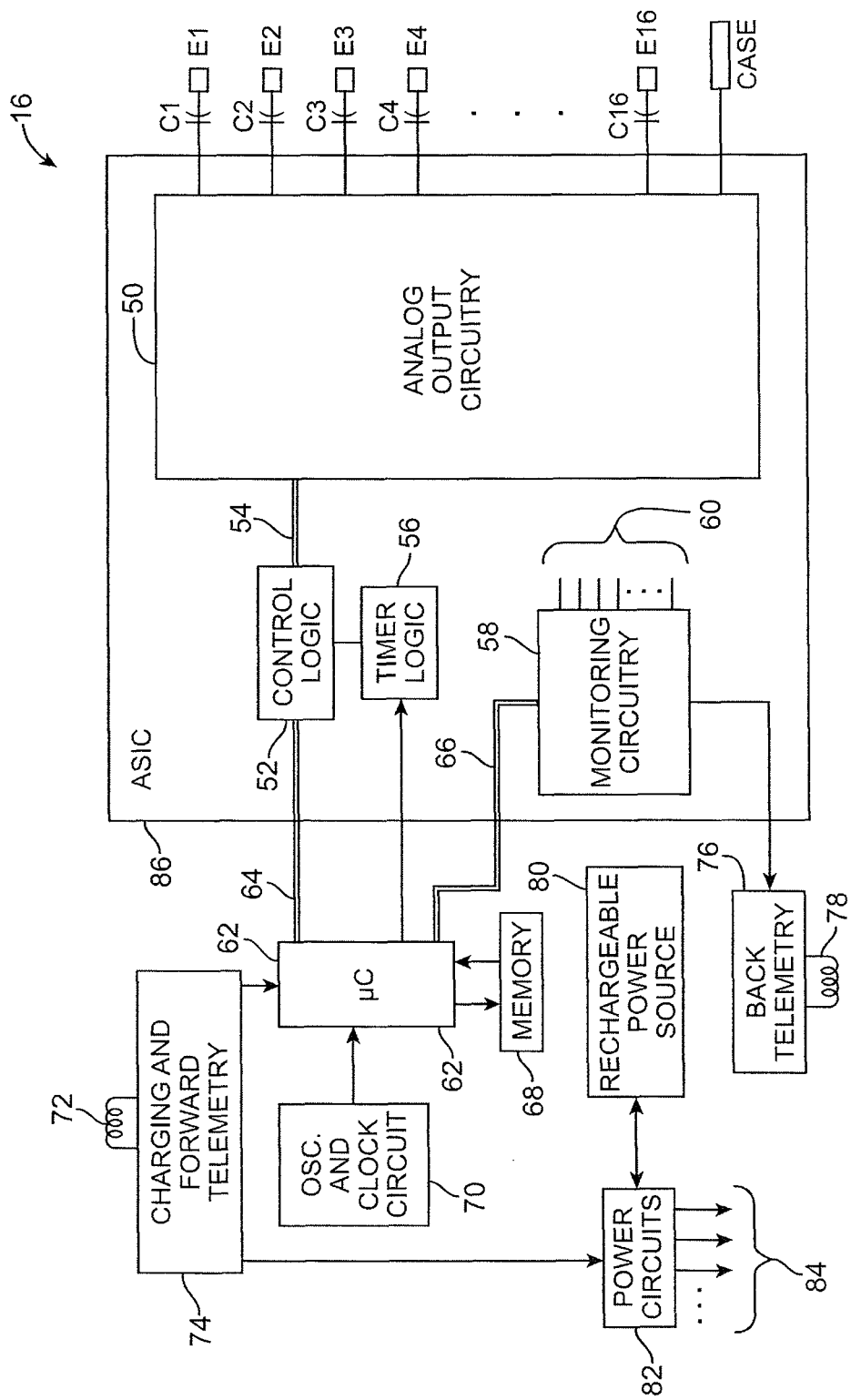
FIG. 4 is a block diagram of the internal components of the IPG of FIG. 2.

Turning next to FIG. 4, the main internal components of the IPG 16 will now be described. The IPG 16 includes analog output circuitry 50 capable of individually generating electrical stimulation pulses via capacitors C1-C16 at the electrodes 20 (E1-E16) of specified amplitude under control of control logic 52 over data bus 54. The duration of the electrical stimulation (i.e., the width of the stimulation pulses), is controlled by the timer logic circuitry 56. The analog output circuitry 50 may either comprise independently controlled current sources for providing stimulation pulses of a specified and known amperage to or from the electrodes 20, or independently controlled voltage sources for providing stimulation pulses of a specified and known voltage at the electrodes 20. The operation of this analog output circuitry, including alternative embodiments of suitable output circuitry for performing the same function of generating stimulation pulses of a prescribed amplitude and width, is described more fully in U.S. Pat. Nos. 6,516,227 and 6,993,384, which are expressly incorporated herein by reference.

The IPG 16 further comprises monitoring circuitry 58 for monitoring the status of various nodes or other points 60 throughout the IPG 16, e.g., power supply voltages, temperature, battery voltage, and the like. The monitoring circuitry 58 is also configured for measuring electrical parameter data (e.g., electrode impedance and/or electrode field potential).

Measuring electrode impedance is important, because implanted electrical stimulation systems depend upon the stability of the devices to be able to convey electrical stimulation pulses of known energy to the target tissue to be excited. The target tissue represents a known electrical load into which the electrical energy associated with the stimulation pulse is to be delivered. If the impedance is too high, that suggests the connector 32a and/or lead 12, 14, which connect with the electrode 20 may be open or broken. If the impedance is too low, that suggests that there may be a short circuit somewhere in the connector 32a and/or lead 12, 14. In either event (too high or too low impedance), the IPG 16 may be unable to perform its intended function.

Measurement of the electrical parameter data also facilitates lead migration detection, as described in U.S. Pat. No. 6,993,384, which has previously been incorporated herein by reference. As will be described in further detail below, electrical parameter data measurements facilitate tracking of the physical activity of the patient. To this end, the monitoring circuitry 58 may include additional filtering circuitry, such as peak detectors, envelope detectors, integrators, etc., for isolating various aspects of the signal resulting from the electrical parameter data measurements, as will be described in further detail below.

Electrical parameter data can be measured using any one of a variety means. For example, the electrical parameter data measurements can be made on a sampled basis during a portion of the time while the electrical stimulus pulse is being applied to the tissue, or immediately subsequent to stimulation, as described in U.S. patent application Ser. No. 10/364,436, entitled "Neural Stimulation System Providing Auto Adjustment of Stimulus Output as a Function of Sensed Impedance," which is expressly incorporated herein by reference. Alternatively, the electrical parameter data measurements can be made independently of the electrical stimulation pulses, such as described in U.S. Pat. Nos. 6,516,227 and 6,993,384, which are expressly incorporated herein by reference.

The IPG 16 further comprises processing circuitry in the form of a microcontroller (μC) 62 that controls the control logic over data bus 64, and obtains status data from the monitoring circuitry 58 via data bus 66. The IPG 16 additionally controls the timer logic 56. The IPG 16 further comprises memory 68 and oscillator and clock circuit 70 coupled to the μC 62. The μC 62, in combination with the memory 68 and oscillator and clock circuit 70, thus comprise a microprocessor system that carries out a program function in accordance with a suitable program stored in the memory 68. Alternatively, for some applications, the function provided by the microprocessor system may be carried out by a suitable state machine.

Thus, the μC 62 generates the necessary control and status signals, which allow the μC 62 to control the operation of the IPG 16 in accordance with a selected operating program and stimulation parameters. In controlling the operation of the IPG 16, the μC 62 is able to individually generate stimulus pulses at the electrodes 20 using the analog output circuitry 60, in combination with the control logic 52 and timer logic 56, thereby allowing each electrode 20 to be paired or grouped with other electrodes 20, including the monopolar case electrode, to control the polarity, amplitude, rate, pulse width and channel through which the current stimulus pulses are provided. The μC 62 facilitates the storage of electrical parameter data measured by the monitoring circuitry 58 within memory 68, and also provides any computational capability needed to analyze such electrical parameter data and/or generate patient activity information.

The IPG 16 further comprises an alternating current (AC) receiving coil 72 for receiving programming data (e.g., the operating program and/or stimulation parameters) from the external programmer 34 in an appropriate modulated carrier signal, and charging and forward telemetry circuitry 74 for demodulating the carrier signal it receives through the AC receiving coil 72 to recover the programming data, which programming data is then stored within the memory 68, or within other memory elements (not shown) distributed throughout the IPG 16.

The IPG 16 further comprises back telemetry circuitry 76 and an alternating current (AC) transmission coil 78 for sending informational data sensed through the monitoring circuitry 58 to the external programmer 34. The back telemetry features of the IPG 16 also allow its status to be checked. For example, when the external programmer 34 initiates a programming session with the IPG 16, the capacity of the battery is telemetered, so that the external programmer can calculate the estimated time to recharge. Any changes made to the current stimulus parameters are confirmed through back telemetry, thereby assuring that such changes have been correctly received and implemented within the implant system. Moreover, upon interrogation by the external programmer 16, all programmable settings stored within the IPG 16 may be uploaded to the external programmer 34. Significantly, the back telemetry features allow raw or processed electrical parameter data and/or patient activity information previously stored in the memory 68 to be downloaded from the IPG 16 to the external programmer 34, which information can be used to track the physical activity of the patient.

The IPG 16 further comprises a rechargeable power source 80 and power circuits 82 for providing the operating power to the IPG 16. The rechargeable power source 80 may, e.g., comprise a lithium-ion or lithium-ion polymer battery. The rechargeable battery 80 provides an unregulated voltage to the power circuits 82. The power circuits 82, in turn, generate the various voltages 84, some of which are regulated and some of which are not, as needed by the various circuits located within the IPG 16. The rechargeable power source 80 is recharged using rectified AC power (or DC power converted from AC power through other means, e.g., efficient AC-to-DC converter circuits, also known as "inverter circuits") received by the AC receiving coil 72. To recharge the power source 80, an external charger (not shown), which generates the AC magnetic field, is placed against, or otherwise adjacent, to the patient's skin over the implanted IPG 16. The AC magnetic field emitted by the external charger induces AC currents in the AC receiving coil 72. The charging and forward telemetry circuitry 74 rectifies the AC current to produce DC current, which is used to charge the power source 80. While the AC receiving coil 72 is described as being used for both wirelessly receiving communications (e.g., programming and control data) and charging energy from the external device, it should be appreciated that the AC receiving coil 72 can be arranged as a dedicated charging coil, while another coil, such as coil 78, can be used for bi-directional telemetry.

As shown in FIG. 4, much of the circuitry included within the IPG 16 may be realized on a single application specific integrated circuit (ASIC) 86. This allows the overall size of the IPG 16 to be quite small, and readily housed within a suitable hermetically-sealed case. Alternatively, most of the circuitry included within the IPG 16 may be located on multiple digital and analog dies, as described in U.S. patent application Ser. No. 11/177,503, filed Jul. 8, 2005, which is incorporated herein by reference in its entirety. For example, a processor chip, such as an application specific integrated circuit (ASIC), can be provided to perform the processing functions with on-board software. An analog IC (AIC) can be provided to perform several tasks necessary for the functionality of the IPG 16, including providing power regulation, stimulus output, impedance measurement and monitoring. A digital IC (DigIC) may be provided to function as the primary interface between the processor IC and analog IC by controlling and changing the stimulus levels and sequences of the current output by the stimulation circuitry in the analog IC when prompted by the processor IC.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described, which functions include not only producing a stimulus current or voltage on selected groups of electrodes, but also the ability to measure electrical parameter data at an activated or non-activated electrode. Such measurements allow impedance to be determined (used with a first embodiment of the invention) or allow electric field potentials to be measured (used with a second embodiment of the invention), as described in more detail below.

Additional details concerning the above-described and other IPGs may be found in U.S. Pat. No. 6,516,227, U.S. Patent Publication No. 2003/0139781, and U.S. patent application Ser. No. 11/138,632, entitled "Low Power Loss Current Digital-to-Analog Converter Used in an Implantable Pulse Generator," which are expressly incorporated herein by reference. It should be noted that rather than an IPG, the SCS system 10 may alternatively utilize an implantable receiver-stimulator (not shown) connected to leads 12, 14. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

As has been indicated, the physical activity of the patient can be tracked by the system 10 based on measured electrical parameter data at the electrodes 20, and in the illustrated embodiments, the measured interelectrode and/or measured field potential. Preferably, the physical activity of the patient is tracked anytime after the leads 12, 14 have been properly positioned within tissue ("proper" positioning varies from patient to patient). Preferably, the interelectrode impedance and/or field potentials are measured in a continuous fashion (either by analog means or digital means with adequate sampling rate (e.g., 20-1000 HZ). The electrodes 20 at which the electrical parameter data is measured are preferably the electrodes 20 that are most sensitive to the patient movement; that is, the electrodes 20 where the electrical parameter data exhibits the highest change (slope) with the activity type to be assessed.

Figure 5:
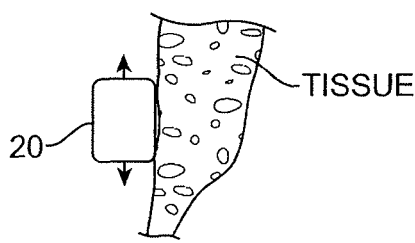
FIG. 5 is a plan view of an electrode of the SCS system of FIG. 1 shown moving a small amount relative to the tissue in response to a small amount of patient activity.
Figure 6:
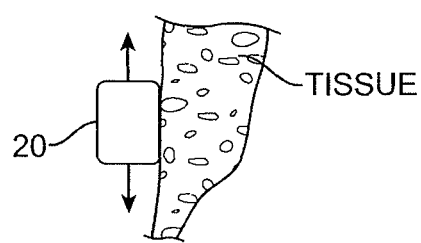
FIG. 6 is a plan view of an electrode of the SCS system of FIG. 1 shown moving a large amount relative to the tissue in response to a large amount of patient activity.

As will be described in further detail below, changes in the measured electrical parameter data (e.g., interelectrode impedance and/or measured field potentials) can be correlated to body movement. In particular, during movements in the body of the patient, the contact surfaces of the electrodes 20 in intimate contact with the tissue of the patient move relative to the tissue and other electrodes 20, thereby causing the measured electrical parameter data to instantaneously change in a manner grossly correlated to the body movements. For example, as illustrated in FIG. 5, an electrode 20 may exhibit very little movement (represented by smaller arrows) relative to the tissue when the patient, e.g., is lying down, whereas, as illustrated in FIG. 6, an electrode 20 may exhibit large movement (represented by larger arrows) relative to the tissue when the patient is, e.g., walking. The electrical parameter data measured at the electrode 20 will accordingly change with the relative movement between the electrode 20 and the tissue, thereby providing an indication of the physical activity of the patient. It should be noted that the electrical energy generated between two electrodes 20 to facilitate the impedance or field potential measurements may be the same energy used to therapeutically stimulate the tissue, or may be generated independently of the electrical stimulation energy; for example, it may be sub-threshold electrical energy that will not cause stimulation or substantially drain the IPG battery.

The interelectrode impedance technique is performed by measuring impedance vectors, which can be defined as impedance values measured between selected pairs of electrodes 20. Notably, the electrodes 20 fit snugly within the epidural space of the spinal column, and because the tissue is conductive, there is an impedance associated therewith that indicates how easily current flows therethrough. The interelectrode impedance may be determined in various ways. For example, a known current (in the case where the analog output circuitry 50 is sourcing current) can be applied between a pair of electrodes 20, a voltage between the electrodes 20 can be measured, and an impedance between the electrodes 20 can be calculated as a ratio of the measured voltage to known current. Or a known voltage (in the case where the analog output circuitry 50 is sourcing voltage) can be applied between a pair of electrodes 20, a current between the electrodes 20 can be measured, and an impedance between the electrodes 20 can be calculated as a ratio of the known voltage to measured current.

The field potential technique is performed by generating an electrical field at selected ones of the electrodes 20 and recording the electrical field at other selected ones of the lead electrodes 20. This may be accomplished in one of a variety of manners. For example, an electrical field may be generated conveying electrical energy to a selected one of the electrodes 20 and returning the electrical energy at the IPG case 34. Alternatively, multipolar configurations (e.g., bipolar or tripolar) may be created between the lead electrodes 20. Or, an electrode that is sutured (or otherwise permanently or temporarily attached (e.g., an adhesive or gel-based electrode) anywhere on the patient's body may be used in place of the case IPG outer case 34 or lead electrodes 20. In either case, while a selected one of the electrodes 20 is activated to generate the electrical field, a selected one of the electrodes 20 (different from the activated electrode) is operated to record the voltage potential of the electrical field.

Figure 7:
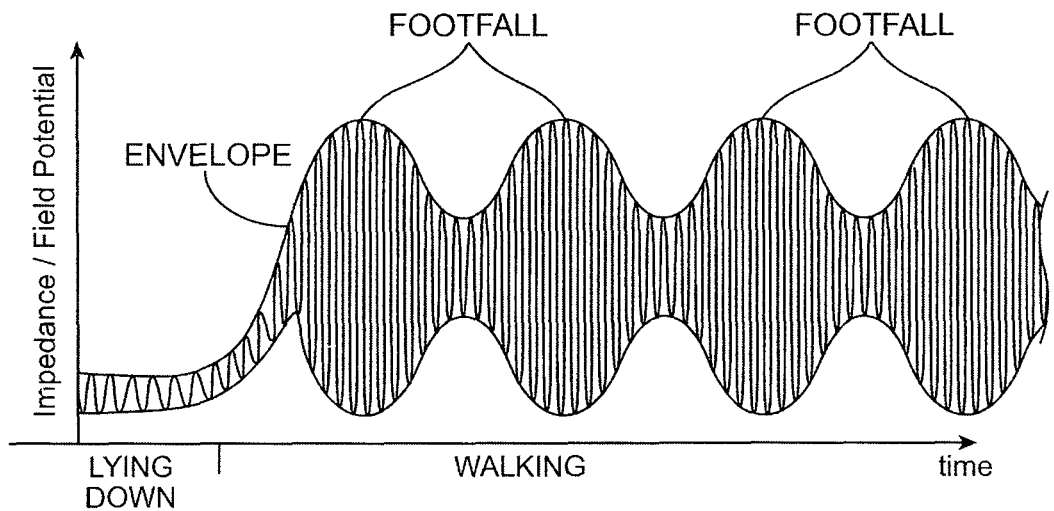
FIG. 7 is a plot of electrical parameter data measured by the SCS system of FIG. 1 over time in response to various physical activities performed by the patient.

As illustrated in FIG. 7, the electrical parameter data measurement will be modulated by the physical activity of the patient to generate a time-varying electrical signal, which by nature can be described as a time-varying, and in particular, an oscillating, electrical noise, since it is rarely clear exactly which tissues or electrodes are changing or in what manner they are changing (i.e., the inverse problem is difficult or impossible to solve in any specific patient).

The term "oscillating" or "oscillate" means a variation around (above and below) a mean, which is not necessarily limited to a square wave or a sine wave. The term "noise" here is merely descriptive, intended to characterize the signal parameter variation. In fact, the variation of this signal actually contains the desired information for inferring patient activity and thus does not meet the definition of 'noise' as undesirable information or 'no information' per se. Despite the fact that the measured electrical parameter data is modulated to generate electrical noise, certain features of the electrical noise can still be analyzed to track the physical activity of the patient, whether such physical activity constitutes walking/running (i.e., footfalls) or postural changes (e.g., trunk twisting, bending, etc.).

Such analysis can be performed during the period of time during which therapeutic stimulation is applied to the patient to provide an indication of the efficacy of the stimulation. For the purposes of this specification, the period of time in which therapeutic stimulation is applied to the patient does not necessarily mean that the stimulation is applied continuously during that period of time; rather that the therapeutic stimulation is being applied to the patient as needed or desired during the period of time. The analysis of the measured electrical parameter data can be performed internally in the IPG 16 (i.e., by the μC 62), or by the external programmer 12 or other external processing device after downloading the measured electrical parameter data from the IPG 16 in combination with any computational or analytical functions performed by the IPG 16.

In one method, tracking of the physical activity of the patient comprises estimating the extent of the physical activity level (expenditure of energy) of the patient. The more physically active the patient during the time period in which therapeutic stimulation is applied (at least during waking hours), the more it can be assumed that the therapeutic stimulation is effective, whereas the less physically active the patient during such time period, the more it can be assumed that the therapeutic stimulation is not effective. Of course, the correlation between the physical activity level and the efficacy of the therapeutic stimulation will be highly dependent on the normal physical activity performed by the patient. As such, correlation between the physical activity level and the efficacy of the therapeutic stimulation will need to be normalized for each patient.

One of the features of the measured electrical parameter data that can be detected to estimate the extent of the physical activity level is the magnitude of the measured electrical parameter data. Such magnitude can be measured in one of a variety of manners. For example, the peak-to-peak amplitude of the measured electrical parameter data can be detected to determine its magnitude, and thus, estimate the extent of the physical activity level of the patient. That is, the greater the physical activity level of the patient, the higher the peak-to-peak amplitude of the measured electrical parameter data will be. Thus, as illustrated in FIG. 7, a relatively low peak-to-peak amplitude may indicate that the patient is lying down or otherwise expending little physical energy, whereas a relatively high peak-to-peak amplitude may indicate that the patient is walking, running, or otherwise expending a lot of physical energy.

Alternatively, rather than analyzing the peak-to-peak amplitude, the energy of the measured electrical parameter data (as determined by integrating the electrical noise) can be detected to determine its magnitude, and thus, estimate the extent of the physical activity level of the patient. Thus, a relatively low integrated energy level may indicate that the patient is expending little energy, whereas a relatively high integrated energy level may indicate that the patient is expending a lot of physical energy. As another alternative, an envelope of the measured electrical parameter data may alternatively be detected to estimate the extent of the activity level of the patient. Thus, a relatively low amplitude of the envelope may indicate that the patient is expending little energy, whereas a relatively high amplitude of the envelope may indicate that the patient is expending a lot of energy.

The measured electrical parameter data may also be analyzed to determine physical events performed by the patient in addition to, or instead, of estimating the physical activity level of the patient. The determined physical events can be used to determine the efficacy of the therapeutic stimulation applied to the patient. For example, if it is determined that the patient is walking or running during the time period in which therapeutic stimulation is applied, it can be assumed that the therapeutic stimulation is effective, whereas if is determined that the patient is continually in a supine position during such time period, it can be assumed that the therapeutic stimulation is not effective.

The determined physical event can also be used to determine whether the physical activity performed by the patient is diurnal or nocturnal. That is, while it can be assumed that diurnal physical activity directly correlates with the efficacy of the therapeutic stimulation applied to the patient, nocturnal physical activity may inversely correlate with the efficacy of the therapeutic stimulation applied to the patient. For example, erratic and sparse body rotations may indicate that the patient is "tossing and turning" in bed, thereby leading one to believe that the therapeutic stimulation is not effective. Thus, if it is determined that the patient is in a supine position during an extended period of time, it can be assumed that any physical activity performed during that time is nocturnal.

The physical events performed by the patient can be determined by analyzing the measured electrical parameter data in any one of a variety of manners. For example, the morphology of the envelope may be analyzed to determine physical events. As shown in FIG. 7, the peaks of the envelope, which correspond to footfalls, may be used to determine that when and how long the patient is walking. As another example, certain physical events performed by the patient may be correlated to the magnitude of the measured electrical parameter data. A specific method of implementing this link is to generate a correlation table ("look-up" table), which may be developed for different body movements, for example. The types of physical events that can be included in the correlation table are those movements normally made during the day, e.g., laying down, walking, jogging, jumping, sitting, twisting, etc. Each of these events may be characterized in the laboratory for each individual patient to generate a personalized look-up table that correlates the physical events with the measured electrical parameter data. After the look-up table is generated, it can be downloaded into the memory 68 of the IPG 16. This look-up table may then be recalled by the μC 62 in the IPG 16 to create a histogram of physical events performed by the patient over a period of time during which the patient is being therapeutically stimulated.

The physical events performed by the patient can also be determined using means other than analysis of the measured electrical parameter data. For example, addition sensors (impedance, activity, accelerometer, etc.) can be used to independently sense the physical events of the patient, such that the magnitude of the measured electrical parameter data can be correlated with different body manipulations. Optionally, the electrical parameter data can be measured on a time-base, such that the data can be analyzed against a clock (not shown) contained with the IPG 16, which may be synchronized to a Greenwich Mea time (GMT)-based clock ("real-time" clock). As in the above example, if the clock indicates that it is nighttime, and erratic and sparse body rotations are measured, then again, these physical events may be attributed to "tossing and turning" in bed.

Figure 8:
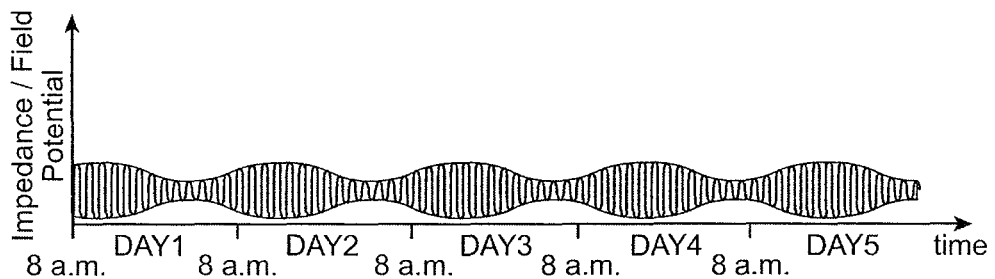
FIG. 8 is a plot of electrical parameter data measured by the SCS system of FIG. 1 over time in response to a Circadian diurnal/nocturnal pattern of the patient.
Figure 9:
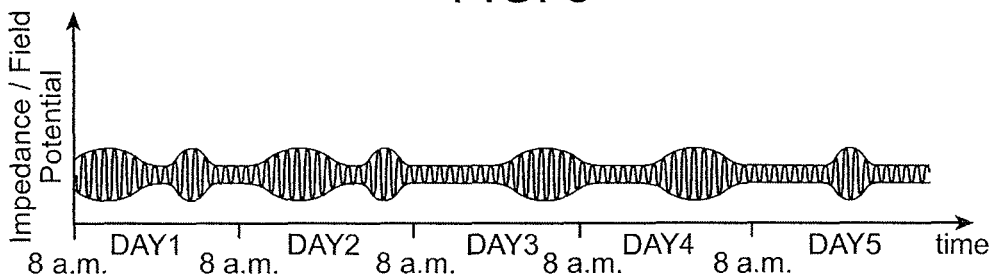
FIG. 9 is a plot of electrical parameter data measured by the SCS system of FIG. 1 over time in response to an erratic diurnal/nocturnal pattern of the patient.

The measured electrical parameter data may be also be analyzed over several days to determine whether the physical activity performed by the patient is diurnal, and thus healthy, or nocturnal, and thus unhealthy. For example, FIG. 8 illustrates an exemplary electrical parameter data measurement taken over several days. As shown, the pattern of the measured electrical parameter data is Circadian in nature; that is, the magnitude of the electrical parameter data consistently increases during a certain period of the day (in this case, approximately between 8 am and 11 pm), and consistently decreases during another period of the day (in this case, approximately between 11 pm and 8 am), indicating that the patient is physically active at daytime and having a restful sleep at nighttime. In contrast, FIG. 9 illustrates another exemplary electrical parameter data measurement taken over several days. As shown, the pattern of the measured electrical parameter data is erratic and inconsistent, indicating that the sleep quality of the patient is lacking.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, comprising:
conveying time-varying electrical energy having an envelope from an implanted tissue stimulation device into tissue of the patient over a period of time, whereby the envelope of the electrical energy is modulated in response to physical activity of the patient;
deriving a time-varying signal containing electrical parameter data from the modulated time-varying electrical energy;
analyzing the time-varying signal; and
tracking the physical activity of the patient during the time period based on the analyzed time-varying signal, wherein the tracked physical activity is indicative of the efficacy of the therapy provided to the patient.

2. The method of claim 1, wherein the electrical energy conveyed from the tissue stimulation device provides therapy to the patient.

3. The method of claim 1, wherein the electrical parameter data is one or both of electrical impedance data or field potential data.

4. The method of claim 1, wherein the time-varying signal analysis comprises determining a magnitude of the time-varying signal.

5. The method of claim 4, wherein the time-varying signal magnitude determination comprises detecting peak-to-peak amplitude values of the time-varying signal, detecting an energy of the time-varying signal, or detecting an envelope of the time-varying signal.

6. The method of claim 1, wherein the time-varying signal analysis comprises determining a morphology of the time-varying signal.

7. The method of claim 6, wherein the time-varying signal morphology determination comprises detecting an envelope of the time-varying signal.

8. The method of claim 1, wherein tracking the physical activity of the patient comprises tracking the physical activity level of the patient.

9. The method of claim 8, wherein determining the physical activity level of the patient comprises determining whether the physical activity level is relatively high or the physical activity level is relatively low.

10. The method of claim 1, wherein tracking the physical activity of the patient comprises tracking the different types of physical events performed by the patient.

11. The method of claim 10, wherein the different types of physical events performed by the patient comprise at least two of laying down, walking, jogging, jumping, sitting, and twisting.

12. The method of claim 10, wherein the different types of physical events are stored in a look-up table respectively correlated to previously measured reference electrical parameter data, wherein tracking the different types of physical events performed by the patient comprises comparing the measuring electrical parameter data to the reference electrical parameter data stored in the look-up table, and determining the different types of physical activity during the time period based on the comparison.

13. The method of claim 1, further comprising modifying therapy provided to the patient by the stimulation device based on the tracked physical activity.

14. The method of claim 1, wherein the time-varying signal is an oscillating signal.

15. The method of claim 1, further comprising determining whether the conveyed electrical energy is effective based on the tracked physical activity of the patient.

16. The method of claim 1, wherein tracking the physical activity of the patient comprises tracking the time that physical activity is performed by the patient.

17. The method of claim 16, wherein tracking the time that physical activity is performed by the patient comprises determining whether the physical activity is performed by the patient during a first time period of a 24-hour day or performed by the patient during a second time period of the 24-hour day.

18. The method of claim 17, wherein the first time period is a daytime and the second time period is a nighttime.

19. The method of claim 16, wherein tracking the time that physical activity is performed by the patient comprises determining whether the physical activity is Circadian in nature.

20. The method of claim 1, wherein the patient activity is indicative of whether the therapy provided to the patient treats pain.

21. The method of claim 1, wherein the patient activity is one or both of a footfall and a postural change.

22. The method of claim 1, wherein tracking the physical activity of the patient comprises tracking a time at which physical activity is performed by the patient.

23. A tissue stimulation system, comprising:
an implantable electrode lead;
an implantable electrical stimulation device configured for being coupled to the electrode lead, the electrical stimulation device configured for conveying time-varying electrical energy from the electrode lead into tissue of a patient over a period of time, the time-varying electrical energy having an envelope capable of being modulated in response to physical activity of the patient, the electrical stimulation device further configured for deriving a time-varying signal containing electrical parameter data from the electrical energy conveyed into the tissue of the patient; and
a processing device configured for analyzing the time-varying signal, and tracking the physical activity of the patient during the time period based on the analyzed time-varying signal, wherein the tracked physical activity is indicative of the efficacy of the therapy provided to the patient.

24. The system of claim 23, wherein the stimulation device is configured for conveying the electrical energy from the implanted from the electrode lead to provide therapy to the patient.

25. The system of claim 23, wherein the electrical parameter data is one or both of electrical impedance data or field potential data.

26. The system of claim 23, wherein the processing device is the stimulation device.

27. The system of claim 23, wherein the processing device is an external programmer configured for communicating with the stimulation device.

28. The system of claim 23, wherein the time-varying signal analysis comprises determining a magnitude of the time-varying signal.

29. The system of claim 28, wherein the time-varying signal magnitude determination comprises detecting peak-to-peak amplitude values of the time-varying signal, detecting an energy of the time-varying signal, or detecting an envelope of the time-varying signal.

30. The system of claim 23, wherein the time-varying signal analysis comprises determining a morphology of the time-varying signal.

31. The system of claim 30, wherein the time-varying signal morphology determination comprises detecting an envelope of the time-varying signal.

32. The system of claim 23, wherein tracking the physical activity of the patient comprises tracking the physical activity level of the patient.

33. The system of claim 32, wherein determining the physical activity level of the patient comprises determining whether the physical activity level is relatively high or the physical activity level is relatively low.

34. The system of claim 23, wherein tracking the physical activity of the patient comprises tracking the physical events performed by the patient.

35. The system of claim 34, wherein the different types of physical events performed by the patient comprise at least two of laying down, walking, jogging, jumping, sitting, and twisting.

36. The system of claim 34, further comprising a look-up table storing the different types of physical events respectively correlated to previously measured reference electrical parameter data, wherein tracking the different types of physical events performed by the patient comprises comparing the measuring electrical parameter data to the reference electrical parameter data stored in the look-up table, and determining the different types of physical activity during the time period based on the comparison.

37. The system of claim 23, wherein the time-varying signal is an oscillating signal.

38. The system of claim 23, wherein the processing device is further configured for determining whether the conveyed electrical energy is effective based on the tracked physical activity of the patient.

39. The system of claim 23, wherein tracking the physical activity of the patient comprises tracking the time that physical activity is performed by the patient.

40. The system of claim 39, wherein tracking the time that physical activity is performed by the patient comprises determining whether the physical activity is performed by the patient during a first time period of a 24-hour day or performed by the patient during a second time period of the 24-hour day.

41. The system of claim 40, wherein the first time period is a daytime and the second time period is a nighttime.

42. The system of claim 39, wherein tracking the time that physical activity is performed by the patient comprises determining whether the physical activity is Circadian in nature.

43. The system of claim 23, wherein the patient activity is indicative of whether the therapy provided to the patient treats pain.

44. The system of claim 23, wherein the patient activity is one or both of a footfall and a postural change.

45. The system of claim 23, wherein tracking the physical activity of the patient comprises tracking a time at which physical activity is performed by the patient.

* * * * *